United States Patent [19]
Cabrera et al.

[11] Patent Number: 4,653,719
[45] Date of Patent: Mar. 31, 1987

[54] FLUID CONDUIT AND PINCH VALVE FOR USE THEREWITH

[75] Inventors: Pedro P. Cabrera; Glenn D. Talbot, both of Miami, Fla.

[73] Assignee: Coulter Electronics, Inc., Hialeah, Fla.

[21] Appl. No.: 747,426

[22] Filed: Jun. 21, 1985

[51] Int. Cl.⁴ ............................................. F16L 55/14
[52] U.S. Cl. ........................................... 251/7; 251/4; 251/5
[58] Field of Search .................. 251/4, 5, 7–10

[56] References Cited

U.S. PATENT DOCUMENTS

| 3,882,899 | 5/1975 | Ginsberg et al. | 251/7 |
| 4,172,580 | 10/1979 | Raftis et al. | 251/8 |

FOREIGN PATENT DOCUMENTS

| 556451 | 2/1957 | Italy | 251/8 |
| 2079410 | 1/1982 | United Kingdom | 251/10 |

*Primary Examiner*—Martin P. Schwadron
*Assistant Examiner*—Sheri M. Novack
*Attorney, Agent, or Firm*—Silverman, Cass, Singer & Winburn, Ltd.

[57] ABSTRACT

A molded flexible fluid conduit and a make/before break pinch valve including a slidably movable pressure member spring biased normally against said conduit in closed condition of the valve, said conduit including a pair of elongate longitudinal unitary purchase formations capable of cooperating with slots carried by the valve whereby the conduit forcibly is pulled or stretched in diametrically opposed directions upon actuation of the valve subsequent to periods of closure so as to force the conduit open to permit flow.

8 Claims, 7 Drawing Figures

FLUID CONDUIT AND PINCH VALVE FOR USE THEREWITH

CROSS-REFERENCE TO RELATED PATENTS

This application is directed to improvements upon the subject matter or U.S. Pat. No. 3,882,899 entitled PINCH VALVE CONSTRUCTION, granted May 13, 1975 to Ginsberg et al and U.S. Pat. No. 3,932,065, entitled PNEUMATICALLY CONTROLLED LIQUID TRANSFER SYSTEM, granted Jan. 13, 1976 to Ginsberg et al, the subject matter of each said patent being incorporated by reference herein as a part of this application for the disclosure contained therein.

BACKGROUND OF THE INVENTION

This invention relates generally to fluid flow control systems incorporating pinch valves through which fluid conduits are threaded and the valves operated alternatively to compress the conduit preventing flow and to release the conduit permitting flow.

More particularly, the invention provides a molded elastomeric flexible conduit having outwardly extending purchase means unitary therewith and adapted to be cooperatively coupled to suitable means carried by the valve to enable spreading of the tube when the valve was operated to permit flow subsequent to retention of the conduit in pinched, compressed condition. When the conduit is compressed for a prolonged duration, its elastomeric memory normally to return to the open condition is overcome. The pinched conduit remains closed, or at least partially closed, notwithstanding the relief of the compressive force. The conduit also can become stuck together so as to resist opening when same is desired.

The art has provided many different types of apparatus to perform automated analysis, with many resolutions of problems inherent in varying degree with the classical analytical methods. Many types involve the transfer of liquid in such a manner as to provide quantitatively accurate dilutions and physical transfer of precise volumes of liquid from one location to others.

Difficulties are encountered in switching from one flow path to another. One transfer system involves the use of check valves which are normally one way directional flow valves. Such valves are subject to sealing or seating problems which may be caused by sedimentary buildup formed upon the sealing mechanism. Thus error is introduced due to the extra fluid flow past the sealing location. Other problems are encountered, such as backlash occurring due to time delay between pressure change to close the valve and the time the valve actually closes. Here, more liquid than desired may be permitted past the valve before it has an opportunity or the time within which fully to close off flow. Swelling is another general problem encountered with many of the known check valve structures.

In U.S. Pat. Nos. 3,882,889 and 3,932,065, a solution was offered to the above mentioned problems. There was provided a pneumatically operated pinch valve of the make-before-break type operable upon flexible conduit paths defined by flexible conduits. A valve shell or housing was provided with piston means slidable therein laterally. The conduits were passed through a suitable window formed in the shell and introduced into the path of the pistons. A stationary post also was provided cooperating with at least one of the pistons to stop flow in a conduit passed therebetween.

Notwithstanding the substantial benefit provided by the patented pinch valve and fluid transfer system employing such structures, problems have been encountered which were not fully addressed heretofore.

As mentioned earlier, the flexible conduits generally are formed of elastomeric plastic tubing. The elastomeric tubing possesses a memory to maintain its tubular configuration allowing passage therethrough. The memory normally causes the tubing to return to its open condition after it has been compressed, for example, as by pinching, for a prolonged time period. If compressed, the tubing loses its memory and fails quickly to return to its open condition after prolonged compression. Cold flow may be at least partially responsible for the tube's loss of memory when compressed for a prolonged time period. The loss of memory often is neither predictable nor desirable. The tube can become stuck in closed condition due to the fluid being transported therein.

Pinch valve structures often included a manual override in the form of cam-lock arrangement whereby the valve could be placed in inoperative condition, the conduits remaining open. Although the functional advantages of this proposed solution were satisfactory using a cam-lock arrangement but added increased fabrication and assembly costs. Further, there are situations where one desires to maintain the flexible conduits, one or more thereof, in pinched closed condition for a prolonged duration. Yet when operation is desired, instantaneous response is desired.

SUMMARY OF THE INVENTION

A molded flexible conduit is provided with unitary diametrically opposed longitudinal formations extending outwardly of the circumferential surface of said conduit. The conduit is capable of being coupled to a pinch valve which includes means for alternatively compressing the conduit closed and releasing the conduit to permit passage of fluid therethrough. Because of the possible sticking of the interior wall of the tube together closing the passage or perhaps the result of loss of memory while compressed, say for a prolonged duration, means are provided on said valve for engaging said formations to enable the conduit to be pulled apart in opposite directions when the valve is operated to permit flow therethrough.

DESCRIPTION OF A PREFERRED EMBODIMENT

The invention is intended for use with fluid flow systems employing flexible conduits defining fluid paths and which further employ pinch valves selectively operated to direct flow of fluids along said paths from one location to another.

The pinch valves employed comprise the make-before-break type such as disclosed in U.S. Pat. Nos. 3,932,065 and 3,882,899 and include piston means operative upon flexible conduits arranged in their path serially selectively to compress one or the other or both of said flexible conduits. The pistons slide with the valve to press the conduit against a stationary member also in the valve compressing the conduit and effecting cessation of flow.

The conduit, arranged transversely across the path of the pistons, is formed of elastomeric material and normally has elastomeric memory to return to its tubular open condition after being compressed. However, it has been found that the elastomeric memory may be lost at least temporarily when the conduit has been compressed for a prolonged duration.

The problem encountered may be manifested by the conduit wall sticking to itself to close off flow or this phenomenon may arise due to the softening of the conduit material or the mixture of the material from which the conduit is formed or the fluids traversing same.

The invention resides in the provision of means for forcing the tube into open condition during operation of the valve, even after a prolonged period when the tube is pinched closed. Means are provided to pull the tube diametrically in opposed directions in the course of the operation of the valve positively to assure normal fluid flow even after a long period of inactivity.

Figure 1:
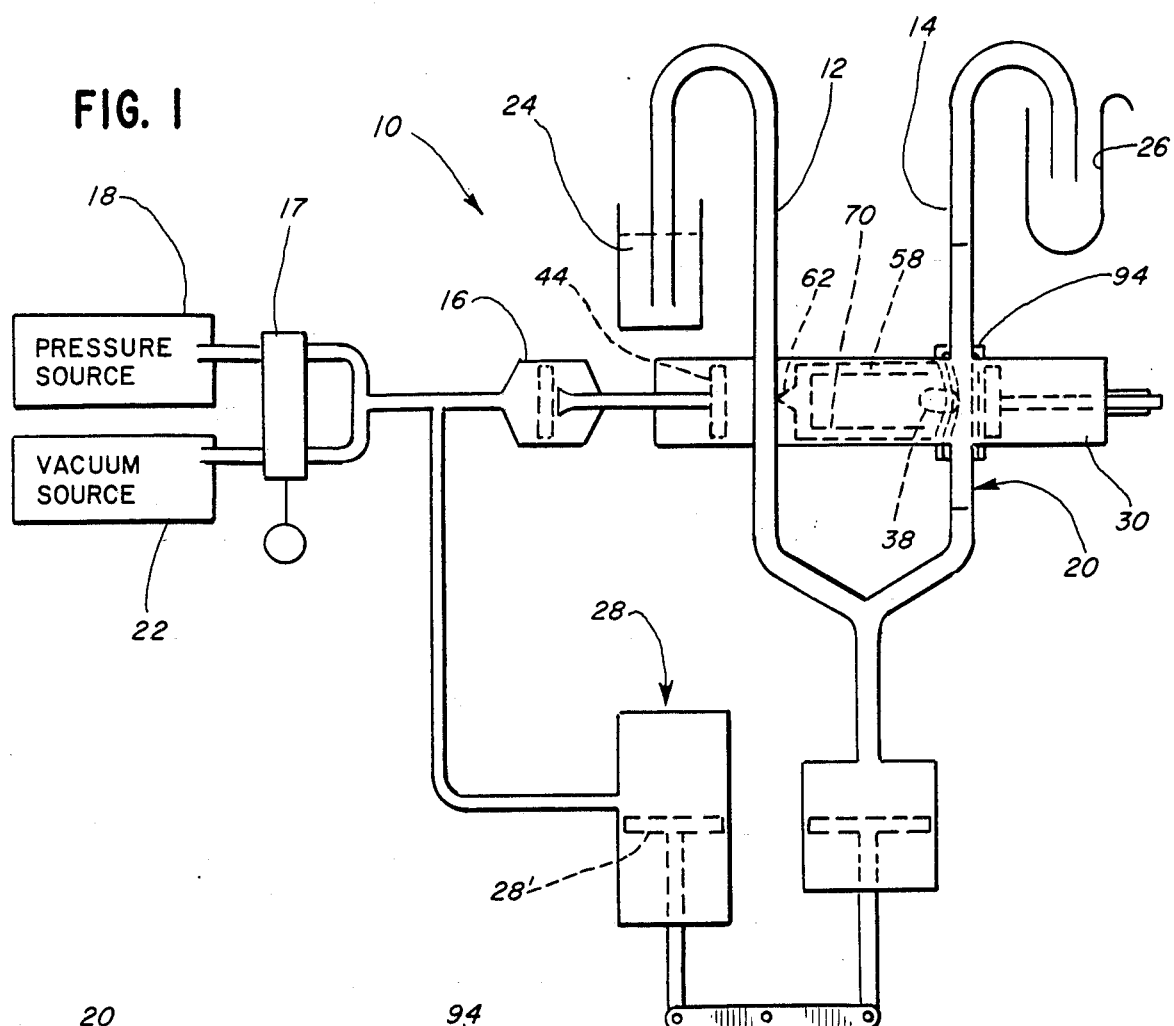
FIG. 1 is a diagrammatic representation of the fluid system showing use of the invention therewith.
Figure 2:
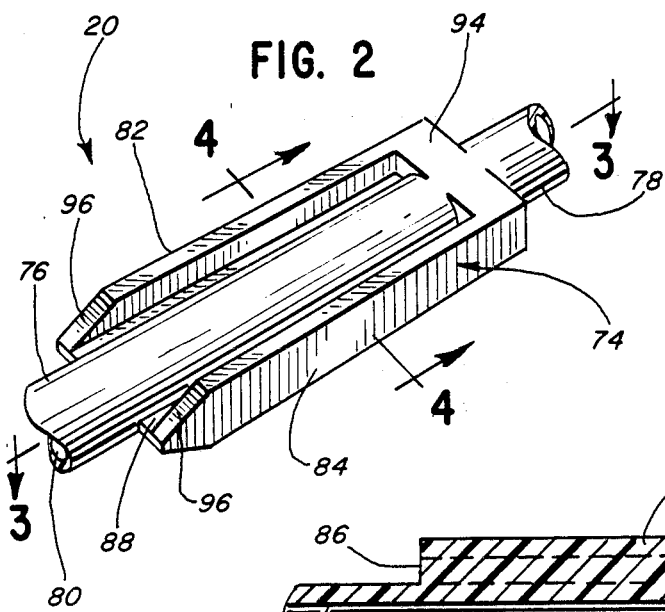
FIG. 2 is a perspective view of the molded fluid conduit constructed according to the invention.
Figure 4:
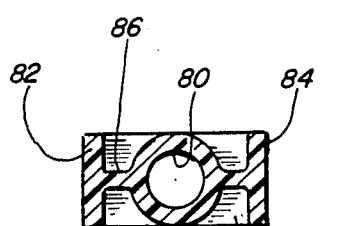
FIG. 4 is a transverse sectional view taken along lines 4—4 of FIG. 2.
Figure 3:
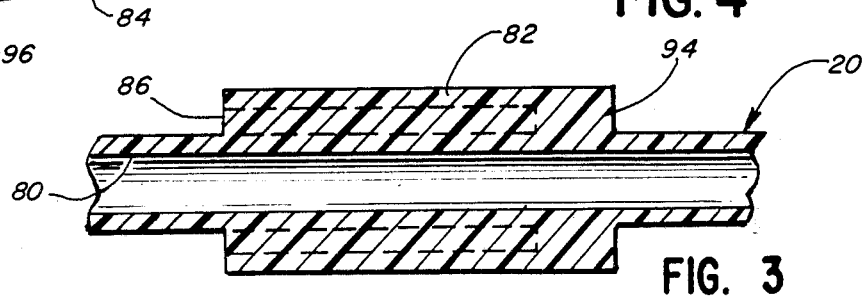
FIG. 3 is a longitudinal sectional view of the conduit taken along line 3—3 of FIG. 2.
Figure 5:
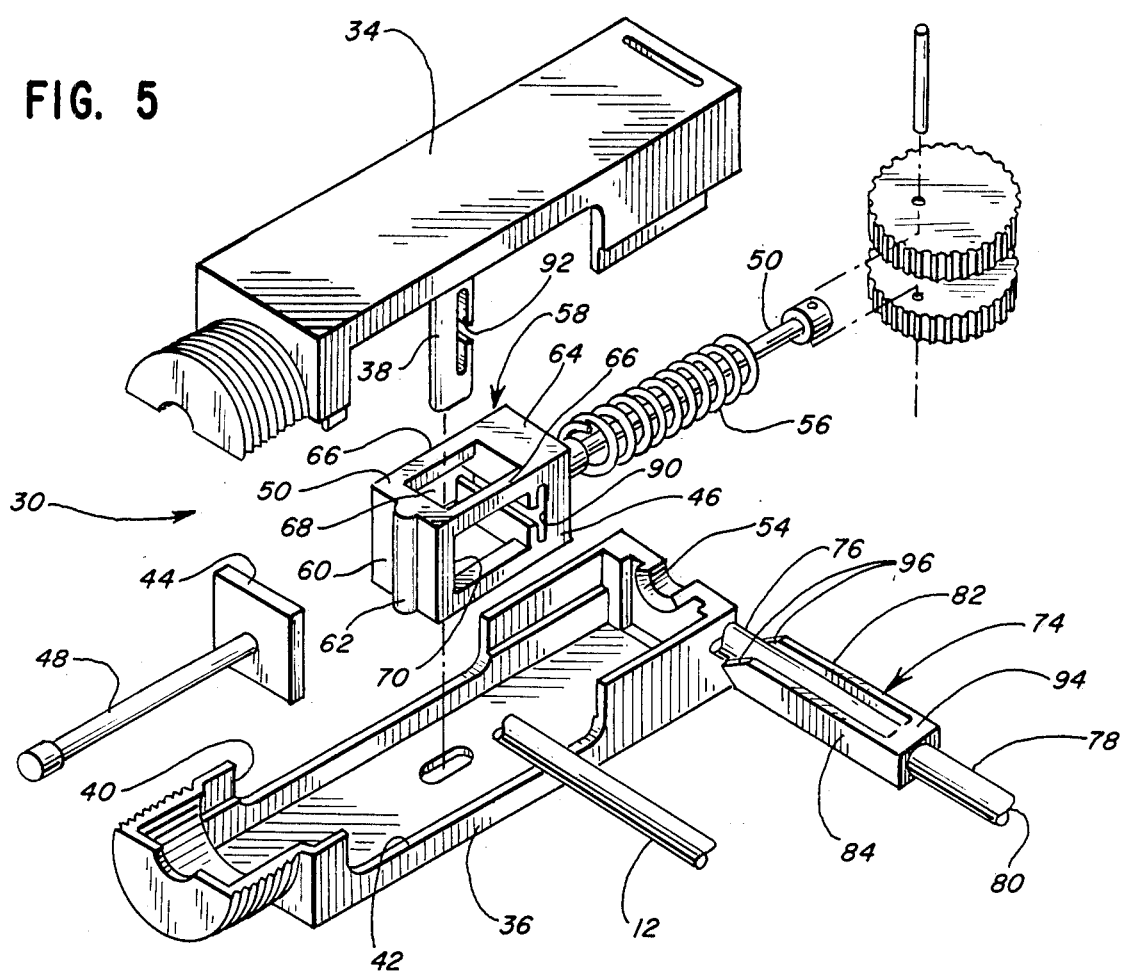
FIG. 5 is an exploded perspective view of a pinch valve employable with the flexible conduit herein described.

Referring now to the drawings, in FIG. 1 a fluid flow system 10 is illustrated diagrammatically, employing the flexible conduit 20 constructed in accordance with the herein invention.

The liquid transfer system 10 includes a pair of flexible conduits, at least one conduit 20 constructed in accordance with the invention. Flexible tubing lines 14 are coupled to the free ends of said conduit 20 to define one of the fluid flow paths for the system 10. The conduit 20 is passed through a single pinch valve 30 and is coupled by way of pneumatic switches 16 and 17 to respective pressure and vacuum sources 18,22 respectively. One of the lines 12 is coupled to a source 24 of liquid while conduit 20 is coupled by line 14 to a delivery location represented by vessel 26. The pneumatic switch 16 selectively controls the actuation of the valve 30 by way of actuating piston 28' of piston/cylinder 28.

Figure 6:
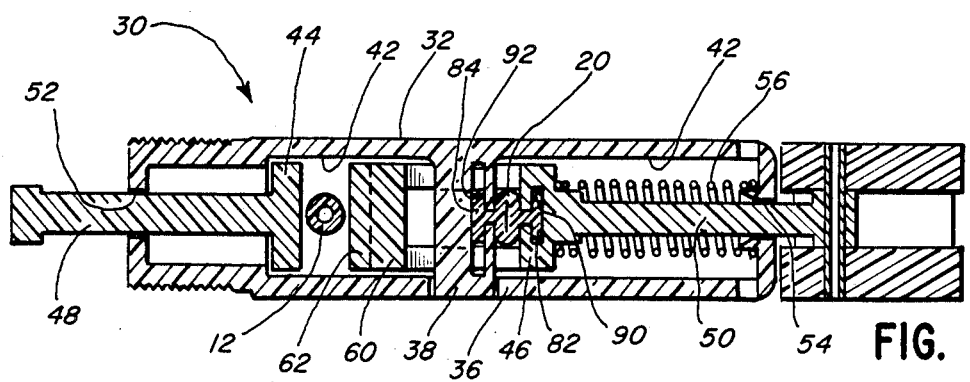
FIG. 6 is a longitudinal sectional view of the assembled pinch valve of FIG. 5 illustrating the pinch valve in the condition assumed just prior to its operation in the fluid system represented by FIG. 1.
Figure 7:
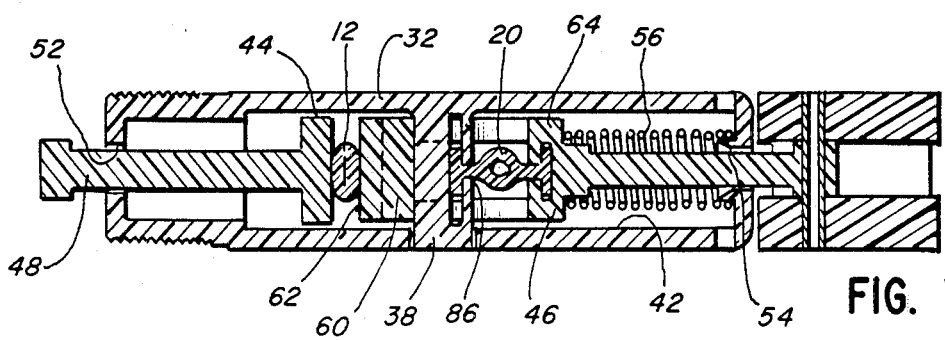
FIG. 7 is a sectional view similar to that of FIG. 6 but illustrating the operation of the invention in reopening the compressed flexible conduit.

The pinch valve 30 is arranged normally with line 12 open and the line 14 closed as represented in FIG. 6. When the valve 30 is actuated, i.e., as by air from the source 18, causing the piston 44 to move to the right, line 12 first is closed with line 14 remaining closed. Then line 14 is opened with line 12 remaining closed. Thereafter, the vacuum is drawn resulting in reversal of the procedure.

The pinch valve 30 comprises a housing 32 formed of a pair of mated shells 34,36 preferably molded of plastic material. Shell 34 has an integral post 38 which is capable of being received tightly in an opening of conforming configuration. The shells are force fitted together. The side walls of the shells have elongate notches 40 which define a window 42 on opposite sides of the housing 32 when assembled to form same.

A pair of pistons 44 and 46 having plungers 48 and 50 are seated respectively within the assembled housing 32. End passageways 52,54 are provided in housing 32 when the shells 34,36 are assembled. Plunger 48 is reciprocable through passageway 52 while plunger 50 is reciprocable through passageway 54.

A helical coil spring 56 is arranged on plunger 50. The piston 46 includes a yoke-like bearing formation 58 defined by a plate 60 carrying an outer rib 62 and a second plate 64 connected to the piston 46 by corner posts 66. The posts define windows 68 and 70. Windows 68,70 are aligned with the window 42 of the housing 32 while the post 38 passes between plates 60,64.

Line 12, here formed of ordinary flexible tubing, is threaded through the windows 42 passing between the piston 44 and the rib 62 of the yoke formation 58. The other conduit 20 is threaded between through windows 70 between the post 38 and the plate 64. Normally the yoke formation 58 is biased by the spring 56 to compress the comduit 20 closed.

In initiating operation of valve 30, the piston 44 is moved laterally to compress conduit 12 against the rib 62 closing conduit 12. Now both conduits 12 as well as conduit 20 are closed. Continued application of force to the plunger 28' forces the yoke formation 58 laterally further to the right, as illustrated, to overcome the bias of the spring 56 whereby to pull apart the conduit 20 diametrically, opening the closed conduit 20. The conduit 12 remains compressed in closed condition.

Drawing vacuum, the force applied to the piston 44 causes the yoke formation 58 to return along its prior path toward its initiate condition, moving laterally to the left. Again, both conduits 12 and 20 are closed until the initiate condition is reached where conduit 12 is open.

In the event conventional flexible tubing conduit used prior to the invention is maintained in a closed or pinched condition for an extended time period, their elastomeric memory, which would cause the conventional conduit to return to an open condition, upon release of the compressive force, is lost or at least reduced in effectiveness with the result that the pinched conduit remains closed, or at least partially closed, and flow of fluid therethrough stopped, or at least restricted. Also, the wall of the collapsed tube may simply be stuck together, perhaps as a result of softening, swelling perhaps due to the effect of the concerned fluids on the conduit material or other factors.

The invention herein is directed toward relief of this problem and hence attention is directed presently thereto. The invention provides flexible conduit 20 with a unitary molded body 74 having tubular end portions 76,78 and a continuous, central axial bore 80. The molded body 74 is formed with a pair of diametrically opposite located flanges 82,84 formed simultaneously with body 74. The flanges 82,84 each extend longitudinally and parallel along a substantial length of the body 74. The flanges are of T-shaped cross-section, with the crossbar 86 of each T extending parallel both to the central axis of bore 80 and to each other, connection being made to the tubular portion of body 74 by short leg 88 of said flanges 82,84.

The plate 64 is formed with a T-shaped slot 90 of size and configuration to accommodate one flange 82 of the T-shaped flanges 82,84 of the conduit 20. The post 38 of valve 30 also is provided with a T-slot 92 of cross-sec tional configuration conforming to the flange 84. When the conduit 20 is passed slidably through the valve windows, the T-flanges are threaded simultaneously through the respective passages 90,92. A unitary stop 94 of generally rectangular configuration is provided at one end of flanges 82,84 to prevent continued passage of the conduit 20 through the valve. When the piston is slidably returned toward the initiate condition of the pinch valve, one flange 84 is held stationary while the piston pulls upon the other flange 82, crossbar 86 thereof being engaged within the slot 90 to pull the conduit 20 apart in a diametrically opposed direction positively assuring that the conduit 20 will return to its open condition regardless of the duration it had remained pinched closed or if the tube is stuck in pinched or closed condition. The length of the formations is selected such as to distribute any tension along the tube as well as to easily guide the formations 82,84 through the respective slots. The formations should be long enough slidably to slip through the respective T-slots. Formations which are too short cause the force to be exercised over a small area of the tube length, thus effecting considerable strain on the connecting flange more likely to result in tearing off of the formation from the tube and/or causing a breach of the wall when pulling force is exercised thereon in opening the tube. The formation can be grasped and pulled to assure full opening of the axial passage thereof. Means to hold one side of the body immobile while pulling on the opposite side may be provided by said opposite formations, one or each of which is to be pulled manually.

The line defining the path of fluid flow through the system is coupled to the free ends of the conduit 20. Bevelled formations 96 can be provided at the free ends of the flanges 82,84 to ease and guide the said flanges through the slots 90,92.

It should be understood that the flexible conduit of the invention also can function in lieu of conduit 12 and, as well, that although the invention has been described as employed in conjunction (combination) with a make-before-break pinch valve having a pair of conduits therethrough, the flexible conduit of the invention is equally useful in combination with a pinch valve operating only between open and closed condition with only one conduit threaded therethrough or even with a valve operating upon more than two conduits.

What is claimed is:

1. In combination, a pinch valve for controlling the passage of fluids along flow path and a unitary molded flexible conduit having a uniform axial small bore for defining said flow path through said valve, said pinch valve operable only between full flow and cease flow conditons, said pinch valve including a stationary portion and reciprocable piston means therewithin, said piston means being slidably movable reciprocably in one direction toward the stationary portion to compress the flexible conduit closed to flow therethrough and in the opposite direction sufficient to open full flow, said flexible conduit being disposed slidably through the pinch valve with a portion of the conduit across the width of the pinch valve and in the path of said piston means in normally fully open condition, slot means formed in both said piston means and said stationary portion and means operable to effect said slidable movement of said piston means, outwardly extending longitudinal elongate ear means formed unitary on diametrically opposed portions of the outer circumferential wall of said flexible conduit, said ear means being drawn through said slot means with the conduit when the conduit is passed through the pinch valve across said path and through the pinch valve, said ear means extending at least co-extensive with that portion of the conduit within the pinch valve whereby uniformly to distribute the force exercised upon the ear means at least over the portion of the conduit within the pinch valve when the piston means is moved in said opposite direction to force reopening of said pinched conduit.

2. The combination as claimed in claim 1 and a stop formation at one end of said ear means for limiting passage of said ear means through the slot means during drawing of the conduit therethrough.

3. The combination as claimed in claim 1 wherein said ear means comprise a pair of diametrically opposed outwardly extending elongate T-formations longitudinally directed along a portion of the length of said conduit at least equal to the portion thereof disposed within the pinch valve.

4. The combination as claimed in claim 1 in which said slot means comprise slots having a configuration conforming to that of said ear means.

5. The combination as claimed in claim 3 wherein each T-formation comprises a radial elongate flange unitary with the outer circumferential wall of said conduit and a crossbar carried at the free end of the flange coextensive thereof and extending axially parallel to the conduit, said crossbars being disposed normal to the respective radial flange and parallel one to the other.

6. The combination as claimed in claim 5 in which said crossbars have bevelled ends to guide slidable passage of said ear means through said slots.

7. A molded flexible small bore conduit for use with a pinch valve of the type having reciprocable piston means operable thereon and slot means formed within said valve and piston means, said conduit formed of elastomeric material and having an outer circumferential wall and a uniform axial bore, having a portion thereof extending within a pinch valve and across the path of reciprocable compression means, the conduit portion being sufficiently flexible for repeated compression and release to close and to open said bore, the release being effected by means capable of exercising positive pulling force simultaneously in diametrically opposed directions generally normal to the longitudinal axis of said elongate longitudinal ear means formed on diametrically opposed portions of said wall and having a substantial length along said wall unitary therewith, said conduit being drawable slidably across the path of the reciprocable piston means in a direction normal to the path thereof and with the ear means through the slot means, the ear means having a configuration substantially conforming to the slot means yet capable of being longitudinally slidable therethrough, said ear means offering the sole purchase between the conduit and the pinch valve for opening and closing the bore, said conduit being manipulatable cyclically only between a condition with the bore fully open and a condition fully compressed with the bore closed.

8. The conduit as claimed in claim 7 wherein said ear means comprise a pair of diametrically opposed coplanar radial flanges extending outward from the outer wall and having free ends, each having a cross bar at said free ends.

* * * * *

UNITED STATES PATENT AND TRADEMARK OFFICE
CERTIFICATE OF CORRECTION

PATENT NO. : 4,653,719

DATED : March 31, 1987

INVENTOR(S) : Pedro P. Cabrera & Glenn D. Talbot

It is certified that error appears in the above-identified patent and that said Letters Patent are hereby corrected as shown below:

Column 6, line 40 through Column 6, line 48 delete "having a portion thereof extending within a pinch valve and across the path of reciprocable compression means, the conduit portion being sufficiently flexible for repeated compression and release to close and to open said bore, the release being effected by means capable of excercising positive pulling force simultaneously in diametrically opposed directions generally normal to the longitudinal axis of said"

Signed and Sealed this

Twenty-second Day of December, 1987

Attest:

DONALD J. QUIGG

*Attesting Officer*    *Commissioner of Patents and Trademarks*